United States Patent [19]

Iwao et al.

[11] 4,374,089
[45] Feb. 15, 1983

[54] CHROMATOGRAPHIC ACCESSORY INCORPORATING INJECTION SWITCH ASSEMBLY

[75] Inventors: Kumiy R. Iwao, Lafayette; James V. Lovie, Chester, both of Calif.

[73] Assignee: Varian Associates, Inc., Palo Alto, Calif.

[21] Appl. No.: 341,396

[22] Filed: Jan. 21, 1982

Related U.S. Application Data

[63] Continuation of Ser. No. 154,188, May 29, 1980, abandoned.

[51] Int. Cl.³ .................... G01N 1/18; G01N 31/06; B01L 11/00
[52] U.S. Cl. ........................ 422/70; 141/83; 141/311 R; 200/153 T; 422/89; 422/99; 422/103; 73/864.86; 73/864.87
[58] Field of Search ............ 422/70, 89, 103, 99; 73/864.86, 864.87, 864.85, 422 GC; 200/153 T, 332, 335, 329; 141/311 R, 83

[56] References Cited

U.S. PATENT DOCUMENTS

| | | | |
|---|---|---|---|
| 2,547,765 | 4/1951 | Lund | 200/153 T X |
| 3,414,385 | 12/1968 | Beroza et al. | 422/99 |
| 3,581,573 | 6/1971 | Purcell et al. | 73/422 GC |
| 3,841,835 | 10/1974 | Kishimoto et al. | 73/422 GC X |
| 3,886,800 | 6/1975 | Boehringer | 141/83 X |
| 3,939,713 | 2/1976 | Estey | 73/422 GC |
| 4,143,254 | 3/1979 | Heyrana | 200/153 T X |
| 4,199,988 | 4/1980 | Riegger | 73/422 GC |

*Primary Examiner*—Kenneth M. Schor
*Attorney, Agent, or Firm*—Stanley Z. Cole; Norman E. Reitz

[57] ABSTRACT

A nut assembly for use on an injection switch for a chromatograph has a nut surrounded by a moveable member which is disposed to travel co-linearly with respect to the axis of the nut. The moveable member is biased so that its upper end extends above the nut to engage the body of a sample syringe. Upon engagement with the sample syringe the moveable member moves downwardly against the bias means. The bias means then triggers the microswitch. Upon withdrawal of the needle of the sample syringe the moveable member returns to its original position.

2 Claims, 4 Drawing Figures

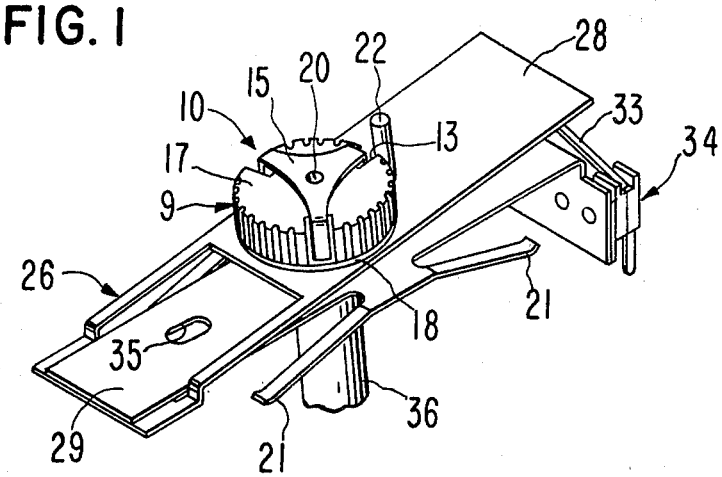
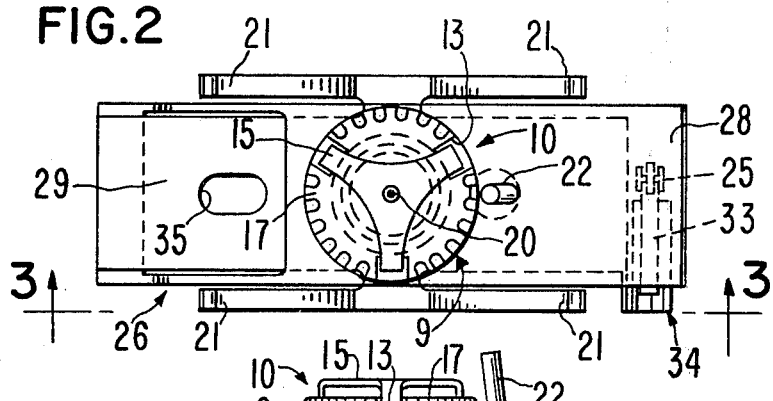
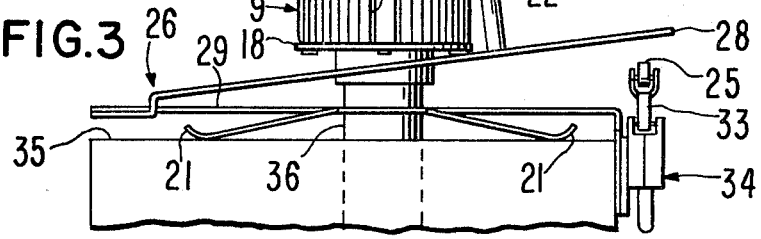
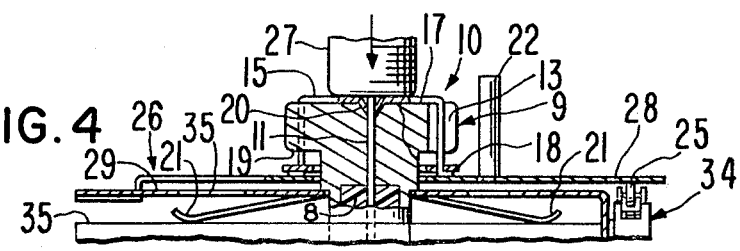

CHROMATOGRAPHIC ACCESSORY INCORPORATING INJECTION SWITCH ASSEMBLY

This application is a continuation, of application Ser. No. 154,188, filed May 29, 1980, now abandoned.

DESCRIPTION

This invention relates to apparatus for activating monitoring or detection equipment upon the injection of a sample into a chromatograph and, more particularly, relates to a chromatographic accessory incorporating an injection switch assembly which initiates such equipment.

In chromatography, samples are introduced to a chromatographic column for separation on the basis of some physical phenomenon such as adsorption. The time for the passage of particular constituent compounds of the sample through the column and the signal amplitude associated with any constituent are carefully monitored. Therefore, it is important to accurately know the time of introduction in order to compare results against standards. In K. Kishimoto, et al., U.S. Pat. No. 3,841,835, "Means for Providing an Information Signal of Sample Introduction in Apparatus for Chemical Analysis", a mechanical linkage is disclosed for mechanically communicating information of the injection of a sample to a microswitch which initiates chemical analysis at the downstream side of the chromatographic column. In addition, in the articles of S. Cram, et al., "Gas-Liquid Chromatographic Analysis with Short-lived Isotopes", *J. of Gas Chromatography*, July 1967, p. 353 and S. Cram, et al., "The Gas Chromatographic Resolution of Gamm-Ray Scintillation Spectra for the Neutron Activation Analysis of Short-lived Isotopes", *J. of Gas Chromatography*, June 1968, p. 305, the use of an optical link to detect the introduction of a sample is illustrated. These injection control mechanisms of the prior art are mechanically complex and costly.

It is therefore an object of the present invention to provide a simple and effective means for activating monitoring and detection equipment upon injection of a sample into a chromatograph.

It is a further object of the present invention to provide a chromatographic accessory incorporating an injection switch assembly.

BRIEF DESCRIPTION OF THE DRAWINGS

For a more complete understanding of the chromatographic accessory incorporating an injection switch assembly of the present invention, reference may be had to the accompanying drawings which are incorporated herein by reference and in which:

FIG. 1 is a perspective view of the chromatographic accessory incorporating an injection switch assembly, including bias means and microswitch;

FIG. 2 is a plan view of FIG. 1;

FIG. 3 is a side view of FIG. 1 illustrating the ready position of the injection switch assembly, including bias means and microswitch; and FIG. 4 is a cross sectional view of FIG. 3 with the moveable member of the injection switch assembly being depressed by a syringe to produce a triggering of the microswitch.

SUMMARY OF THE INVENTION

A chromatographic accessory incorporating an injection switch assembly for use on a chromatograph has a nut surrounded by a moveable member which is disposed to travel co-linearly with respect to the axis of the nut. A bias means biases the moveable member of extend above the nut to permit engagement of the member wih the body of a sample syringe. When the moveable member engages the sample syringe the moveable member is depressed and forces the bias means against the microswitch or other electrical initiation means. Upon removal of the syringe needle the moveable member is returned to its biased position.

DESCRIPTION OF THE PREFERRED EMBODIMENTS

In chromatographs a sample is injected into the inlet end of a packed column with the intention that the constituents of the sample be separated as they pass through the column. The sample may be a gas or a liquid. It is injected into the column in as short a time as possible so that the start of sample flow will be punctiliar and separations will be as sharp as possible. To achieve such punctiliar initiation of flow, syringes are commonly used since they permit accurate determination of sample size, complete delivery of the sample and positive, swift injection. The syringes are typically engaged in a septum during injection in order to guide and hold the needle of the syringe and in order to maintain the integrity of the interior volume of the column. These septums are well known in the art and may consist of rubber or plastic.

The present invention utilizes a spring-biased moveable member which fits around a nut on the injection end of a chromatographic column. At the beginning of insertion of the needle of the syringe through the nut into the septum, contact is made between the body of the syringe and the top of the moveable member. As insertion progresses, the body of the syringe forces the moveable member to move with respect to the end of the column and against the spring bias. The travel of the moveable member is communicated to a microswitch which is turned on to initiate operation of the associated monitoring or detection equipment.

Structure

A nut assembly 10, as seen in FIGS. 1-4, is provided with an axial bore 11 for accommodating a syringe needle. A septum 8 is inserted inside the nut 9 to receive and form a tight fit around the needle of a sample syringe. Typically, the nut assembly 10 is adapted for attachment to a chromatographic column. Attachment may be accomplished by internal or external threading with subsequent connection with complementary mated threads on the column or, alternatively, the nut may be fabricated as an integral part of the end of the chromatographic column. In the embodiment shown, nut assembly 10 consists of a nut 9 held in fixed position with respect to the chromatographic column 36 and a moveable member 15. The nut 9 is provided with a series of notches 13 which serve as tracks for moveable member 15 so that the moveable member may move only co-linearly with respect to the axis of nut 9; there is no rotational degree of freedom. Many variations of this relationship are possible so long as the co-linear slideable relationship is maintained. Moveable member 15 may travel linearly from a position (the ready position) where the bottom 18 rests against the bottom 19 of nut 9 and the position where the top surface of moveable member 15 rests against the top 17 of nut 9. The preponderance of the periphery of nut 9 is exposed so that, if detachably attachable, it may be easily gripped by hand or by a wrench and removed.

From FIGS. 1 and 4 it may noted that a bevelled circular lip 20 is provided for the axial hole through the top surface 17 of nut 9. This is matched by an indentation in the underside of the top surface of moveable member 15. This adds to the positive seating of moveable member 15 and nut assembly 10 in the depressed position and provides a larger target for insertion of the syringe needle.

When nut assembly 10 is used on a chromatographic column, it is intended to be used in conjunction with a bias unit 26 and microswitch 34, all of which together constitute the injection switch assembly of the present invention. The bias unit 26 consists of legs 21 which are integral with base plate 29 which is designed to rest on the top surface of a housing of the chromatograph. Base plate 29 is integrally connected with spring member 28. As seen particularly in FIG. 3, the spring member 28 biases moveable member 15 in the ready position. The bias unit is required in order to raise moveable member 15 to its ready position prior to the introduction of a syringe containing a sample. The strength of the spring should be such that moveable member 15 may readily be pushed downward by the force of a hand holding the syringe or by an autosampler which is performing the injection. Guide post 22 is provided to stabilize and guide the person or machine accomplishing injection.

Operation

When injection into a chromatographic column occurs, a needle is inserted through the central opening in moveable member 15 and downward into the axial bore 11 within nut 9. The needle passes through septum 8 and the sample is introduced into the column. The body 27 of a syringe will engage the upper surface of moveable member 15 immediately prior to injection. As the syringe travels downwardly, moveable member 15 also moves downwardly. As moveable member 15 moves downwardly, it forces its bottom 18 to move against spring member 28. Nut 9 stays in a fixed position with respect to the column since it is either detachably attached to the end of the chromatographic column or is an integral part of the end of the column. Moveable member 15, however, travels downwardly around nut 9. As shown in FIG. 3, the end of spring member 28 will contact roller 25 on arm 33 of microswitch 34 so that by the time spring member 28 is fully depressed, the microswitch will have been thrown. The point in the travel of the spring member 28 at which the microswitch is, in fact, thrown, may be adjusted by the operator. Also, other electrical actuation means may be employed such as optical or Hall effect switches. After injection, the needle and syringe are withdrawn and spring member 28 springs upward thereby returning moveable member 15 to the ready position. The combination of the nut 9 and the bias unit 26 produce an exceedingly simple and reliable means of monitoring the time of introduction of a sample into a chromatograph.

We claim:

1. A chromatographic assembly comprising in combination:

a chromatographic column;

a nut having an axial bore therethrough for accommodating the needle of a sample syringe, said nut having at least three indentations on the exterior thereof which are parallel to said axial bore and which are positioned in equally spaced apart positions around the circumference of said exterior of said nut, said nut being attached to the end of said chromatographic column;

a sheath-like moveable member which is fit around the exterior of said nut, and slides over said nut in the axial direction, the sheath-like moveable member being structured and positioned such that it is prevented from rotational movement with respect to said nut by riding in said at least three identations, said sheath-like moveable member being able to travel between a ready position wherein said sheath-like moveable member has a portion thereof extending above the upper surface of said nut and a depressed position wherein said sheath-like moveable member has been depressed with respect to said upper surface of said nut, said sheath-like moveable member having an opening in its upper surface concentric with said axial bore through said nut to permit the passage of said needle therethrough;

a microswitch electrically connected to monitoring or detection equipment for monitoring or detecting sample separation in said chromatograph column, said microswitch being positioned so as to be contacted by said moveable member when it reaches said depressed position; and bias means engaging the bottom of said moveable member to thereby place said moveable member under tension whereby said moveable member is biased towards said ready position and whereby the depression of said moveable member by said sample syringe works against said tension produced by said bias means and forces said moveable member to contact said microswitch to initiate operation of said monitoring or detection equipment.

2. A chromatographic assembly in accordance with claim 1 wherein said upper surface of said nut has a bevelled indentation around said axial bore and wherein said opening in said moveable member has a bevelled protrusion on the underside of its upper surface for mateable engagement with said bevelled indentation in said upper surface of said nut.

* * * * *